(12) United States Patent
O'Neal et al.

(10) Patent No.: US 8,921,270 B2
(45) Date of Patent: Dec. 30, 2014

(54) METHOD FOR PRE-EMERGENT WEED CONTROL USING TRIAZINE-BASED HERBICIDE

(71) Applicant: Amvac Chemical Corporation, Newport Beach, CA (US)

(72) Inventors: William B. O'Neal, Chapel Hill, NC (US); Richard Porter, Ankeny, IA (US); Peter J. Porpiglia, Putnam Valley, NY (US)

(73) Assignee: Amvac Chemical Corporation, Newport Beach, CA (US)

( * ) Notice: Subject to any disclaimer, the term of this patent is extended or adjusted under 35 U.S.C. 154(b) by 0 days.

(21) Appl. No.: 13/672,629

(22) Filed: Nov. 8, 2012

(65) Prior Publication Data

US 2013/0116123 A1 May 9, 2013

Related U.S. Application Data

(60) Provisional application No. 61/557,277, filed on Nov. 8, 2011.

(51) Int. Cl.
*A01N 43/64* (2006.01)
*A01N 43/68* (2006.01)
*A01N 43/70* (2006.01)

(52) U.S. Cl.
CPC ...................... *A01N 43/70* (2013.01)
USPC ............................ 504/133; 504/232

(58) Field of Classification Search
CPC .............................. A01N 43/64; A01N 43/68
See application file for complete search history.

(56) References Cited

U.S. PATENT DOCUMENTS

| | | | |
|---|---|---|---|
| 4,185,993 A | 1/1980 | Morse | |
| 4,309,210 A | 1/1982 | Quadranti et al. | |
| 7,521,395 B2* | 4/2009 | O'Neal et al. | 504/134 |
| 7,632,782 B2* | 12/2009 | O'Neal et al. | 504/118 |
| 7,897,846 B2* | 3/2011 | Chicoine et al. | 800/300 |
| 2004/0053784 A1 | 3/2004 | Pallett et al. | |
| 2007/0123424 A1 | 5/2007 | Frisch et al. | |
| 2007/0238617 A1 | 10/2007 | Minn et al. | |
| 2008/0319927 A1 | 12/2008 | Dallmier et al. | |
| 2011/0218105 A1* | 9/2011 | Walker | 504/134 |

OTHER PUBLICATIONS

PCT International Application No. PCT/US12/64238, International Search Report dated Jan. 23, 2013.

* cited by examiner

*Primary Examiner* — Alton Pryor
(74) *Attorney, Agent, or Firm* — Pillsbury Winthrop Shaw Pittman LLP

(57) ABSTRACT

Methods for pre-emergent weed control using a triazine-based herbicide are disclosed. Particularly, methods of using ametryn as a pre-emergent herbicide to control weeds in corn crops are disclosed.

32 Claims, 12 Drawing Sheets

| No. | Treat-ment | Rate (lb ai/A) | Timing[1] | Corn Tolerance | | | | | | | |
|---|---|---|---|---|---|---|---|---|---|---|---|
| | | | | % Injury | Height (in) | | #Plants/30 ft | | % Injury | | % Injury |
| | | | | 23DAP[2] | 33DAP | | 33DAP | | 41DAP | | 56DAP |
| 1 | Untreated | | | 0 a | 16 | a | 59 | a | 0 | a | 0 a |
| 2 | Ametryn | 0.8 | 12 Days Preplant | 0 a | 17 | a | 62 | a | 0 | a | 0 a |
| 3 | Ametryn | 1.6 | 12 Days Preplant | 0 a | 17 | a | 54 | a | 0 | a | 0 a |
| 4 | Ametryn | 2.4 | 12 Days Preplant | 0 a | 16 | a | 56 | a | 0 | a | 0 a |
| 5 | Ametryn | 0.8 | 0 Day Preplant | 0 a | 16 | a | 59 | a | 0 | a | 0 a |
| 6 | Ametryn | 1.6 | 0 Day Preplant | 0 a | 16 | a | 52 | a | 0 | a | 0 a |
| 7 | Ametryn | 2.4 | 0 Day Preplant | 0 a | 16 | a | 59 | a | 0 | a | 0 a |
| 8 | Ametryn | 0.8 | PRE | 0 a | 16 | a | 58 | a | 0 | a | 0 a |
| 9 | Ametryn | 1.6 | PRE | 0 a | 16 | a | 57 | a | 0 | a | 0 a |
| 10 | Ametryn | 2.4 | PRE | 0 a | 16 | a | 59 | a | 0 | a | 0 a |

[1] Application timing: Before planting (= "Preplant"), PRE = Preemergence right after planting

[2] DAP indicates days after planting

FIG. 2

| | | | Corn Tolerance | | | | | |
|---|---|---|---|---|---|---|---|---|
| No. | Treatment | Rate (lb ai/A) | Timing[1] | % Stunting 14DAP[2] | | % Stunting 21DAP | | #Plants/30 ft 27DAP | | Height (in) 27DAP | | Yield bu/A | |
| 1 | Untreated | | | 0.0 | f | 0.0 | d | 42.7 | a | 15.333 | bc | 102 | cde |
| 2 | Ametryn | 0.8 | 14 Days Preplant | 0.0 | f | 0.0 | d | 43.3 | a | 17.333 | ab | 114 | a-d |
| 3 | Ametryn | 1.6 | 14 Days Preplant | 1.7 | f | 0.0 | d | 45.7 | a | 17.333 | ab | 142 | a |
| 4 | Ametryn | 2.4 | 14 Days Preplant | 11.7 | c | 1.7 | d | 43.7 | a | 15.667 | bc | 105 | b-e |
| 5 | Ametryn | 0.8 | 2 Day Preplant | 1.7 | f | 0.0 | d | 43.7 | a | 15.667 | bc | 133 | abc |
| 6 | Ametryn | 1.6 | 2 Day Preplant | 10.0 | cd | 0.0 | d | 43.0 | a | 18.667 | a | 134 | abc |
| 7 | Ametryn | 2.4 | 2 Day Preplant | 33.3 | a | 30.0 | a | 42.3 | a | 10.667 | e | 94 | de |
| 8 | Ametryn | 0.8 | PRE | 5.0 | ef | 0.0 | d | 44.3 | a | 16.667 | ab | 113 | a-d |
| 9 | Ametryn | 1.6 | PRE | 6.7 | de | 1.7 | d | 44.7 | a | 15.0 | bc | 120 | a-d |
| 10 | Ametryn | 2.4 | PRE | 20.0 | b | 20.0 | b | 44.0 | a | 12.0 | de | 93 | de |
| 12 | Untreated | | | 0.0 | f | 0.0 | d | 44.0 | a | 18.333 | a | 81 | e |

[1] Application timing: PRE = Preemergence surface after planting; Preplant treatments were incorporated prior to planting.

[2] DAP indicates days after planting

FIG. 3

| No. | Treatment | Rate (lb ai/A) | Timing[1] | Corn Tolerance | | | | | | | | |
|---|---|---|---|---|---|---|---|---|---|---|---|---|
| | | | | % Injury 15DAP[2] | | % Injury 29DAP | | % Injury 41DAP | | Height (in) 15DAP | | |
| | | | | | | | | | | | | |

| No. | Treatment | Rate (lb ai/A) | Timing[1] | % Injury 15DAP[2] | | % Injury 29DAP | | % Injury 41DAP | | Height (in) 15DAP | | Height (in) 29DAP | | Height (in) 41DAP | | #Plants/15 ft 29DAP | |
|---|---|---|---|---|---|---|---|---|---|---|---|---|---|---|---|---|---|
| 1 | Untreated | | | 0.0 | a | 0.0 | a | 2.3 | a | 2.7 | a | 8.5 | a | 24.3 | a | 30.7 | a |
| 2 | Ametryn | 0.8 | 11 Days Preplant | 0.0 | a | 0.0 | a | 0.0 | a | 2.6 | a | 7.3 | a | 26.7 | a | 34.7 | a |
| 3 | Ametryn | 1.6 | 11 Days Preplant | 0.0 | a | 1.7 | a | 1.7 | a | 2.6 | a | 8.5 | a | 26.7 | a | 29.0 | a |
| 4 | Ametryn | 2.4 | 11 Days Preplant | 0.0 | a | 3.3 | a | 3.3 | a | 3.2 | a | 8.3 | a | 25.7 | a | 35.3 | a |
| 5 | Ametryn | 0.8 | 0 Day Preplant | 0.0 | a | 0.0 | a | 2.0 | a | 2.7 | a | 7.3 | a | 24.3 | a | 34.0 | a |
| 6 | Ametryn | 1.6 | 0 Day Preplant | 0.0 | a | 0.0 | a | 0.0 | a | 2.8 | a | 6.7 | a | 23.3 | a | 34.7 | a |
| 7 | Ametryn | 2.4 | 0 Day Preplant | 0.0 | a | 5.0 | a | 5.0 | a | 2.8 | a | 6.7 | a | 21.7 | a | 34.0 | a |
| 8 | Ametryn | 0.8 | PRE | 0.0 | a | 0.0 | a | 0.0 | a | 2.4 | a | 8.4 | a | 25.0 | a | 36.0 | a |
| 9 | Ametryn | 1.6 | PRE | 5.0 | a | 1.0 | a | 0.0 | a | 2.9 | a | 7.8 | a | 26.3 | a | 36.3 | a |
| 10 | Ametryn | 2.4 | PRE | 0.0 | a | 0.0 | a | 0.0 | a | 3.0 | a | 7.4 | a | 24.0 | a | 39.3 | a |

[1] Application timing: PRE = Preemergence right after planting

[2] DAP indicates days after planting

FIG. 4

| No. | Treatment | Rate (lb ai/A) | Timing[1] | % Weed Control | | | |
|---|---|---|---|---|---|---|---|
| | | | | Goosegrass 21DAP[2] | Lambsquater 21DAP | Goosegrass 35DAP | Lambsquater 35DAP |
| 1 | Untreated | | | 0 c | 0 d | 0 c | 0 e |
| 2 | Ametryn | 0.8 | 14 Days Preplant | 60 b | 90 c | 53 b | 75 d |
| 3 | Ametryn | 1.6 | 14 Days Preplant | 90 a | 97 ab | 75 ab | 88 abc |
| 4 | Ametryn | 2.4 | 14 Days Preplant | 95 a | 98 ab | 90 a | 90 abc |
| 5 | Ametryn | 0.8 | 2 Day Preplant | 90 a | 97 ab | 77 ab | 80 cd |
| 6 | Ametryn | 1.6 | 2 Day Preplant | 93 a | 93 bc | 87 a | 87 bcd |
| 7 | Ametryn | 2.4 | 2 Day Preplant | 97 a | 97 ab | 88 a | 92 abc |
| 8 | Ametryn | 0.8 | PRE | 93 a | 93 bc | 82 a | 80 cd |
| 9 | Ametryn | 1.6 | PRE | 97 a | 98 ab | 93 a | 88 abc |
| 10 | Ametryn | 2.4 | PRE | 98 a | 100 a | 97 a | 98 ab |
| 12 | Untreated | | | 0 c | 0 d | 0 c | 0 e |

[1] Application timing: PRE = Preemergence right after planting

[2] DAP indicates days after planting

FIG. 5

|     |                                    | Rate       | % Injury |       | % Weed Control |       |          |       |          |       |          |       |                |       |          |       |
|-----|------------------------------------|------------|----------|-------|----------------|-------|----------|-------|----------|-------|----------|-------|----------------|-------|----------|-------|
|     |                                    |            | Corn     |       | Giant Foxtail  |       | Velvet-leaf |    | Water-hemp |    | Giant Ragweed |  | Morning-glory |     | Cockle-bur |    |
| No. | Treatment                          | (lb ai/A)  | 11DAT[1] |       | 27DAT          |       | 27DAT    |       | 27DAT    |       | 27DAT    |       | 27DAT          |       | 27DAT    |       |
| 1   | Untreated                          |            | 0        | a     | 0              | f     | 0        | e     | 0        | b     | 0        | c     | 0              | c     | 0        | d     |
| 2   | Ametryn                            | 1.20       | 0        | a     | 47             | e     | 78       | cd    | 95       | a     | 77       | b     | 92             | a     | 87       | bc    |
| 3   | Ametryn                            | 1.60       | 0        | a     | 73             | cd    | 82       | cd    | 98       | a     | 85       | ab    | 80             | b     | 75       | c     |
| 4   | Ametryn                            | 2.40       | 0        | a     | 65             | d     | 88       | abc   | 95       | a     | 85       | ab    | 87             | ab    | 97       | ab    |
| 5   | Ametryn Isoxaflutole + safener     | 1.20 0.07  | 0        | a     | 75             | cd    | 97       | a     | 97       | a     | 98       | a     | 93             | a     | 100      | a     |
| 6   | Isoxaflutole + safener             | 0.07       | 0        | a     | 78             | bc    | 95       | ab    | 97       | a     | 95       | ab    | 87             | ab    | 93       | ab    |
|     |                                    |            |          |       | 56DAT          |       | 56DAT    |       | 56DAT    |       | 56DAT    |       | 56DAT          |       | 56DAT    |       |
| 1   | Untreated                          |            |          |       | 0              | d     | 0        | g     | 0        | d     | 0        | c     | 0              | d     | 0        | b     |
| 2   | Ametryn                            | 1.20       |          |       | 13             | cd    | 95       | abc   | 97       | a     | 83       | ab    | 97             | a     | 97       | a     |
| 3   | Ametryn                            | 1.60       |          |       | 20             | c     | 83       | c-f   | 80       | bc    | 90       | ab    | 80             | bc    | 93       | a     |
| 4   | Ametryn                            | 2.40       |          |       | 30             | bc    | 93       | a-d   | 87       | abc   | 75       | ab    | 87             | abc   | 90       | a     |
| 5   | Ametryn and Isoxaflutole + safener | 1.20 0.07  |          |       | 43             | b     | 97       | ab    | 100      | a     | 98       | a     | 87             | abc   | 85       | a     |
| 6   | Isoxaflutole + safener             | 0.07       |          |       | 47             | c     | 93       | a-d   | 93       | abc   | 98       | a     | 77             | c     | 87       | a     |

Application timing: Preemergence broadcast to clean soil surface immediate after corn planting and prior to corn emergence.

[1] Days after indicated application

FIG. 6

| No. | Treatment | Rate (lb ai/A) | Corn (% Injury)[1] 11DAT | | Giant Foxtail 27DAT | | Velvet-leaf 27DAT | | Water-hemp 27DAT | | Giant Ragweed 27DAT | | Morning-glory 27DAT | | Cockle-bur 27DAT | | Giant Foxtail 56DAT | | Velvet-leaf 56DAT | | Morning-glory 56DAT | | Water-hemp 56DAT | | Cockle-bur 56DAT | | Giant Ragweed 56DAT | |
|---|---|---|---|---|---|---|---|---|---|---|---|---|---|---|---|---|---|---|---|---|---|---|---|---|---|---|---|
| 1 | Untreated | | 0 | a | 0 | f | 0 | e | 0 | b | 0 | c | 0 | c | 0 | d | 0 | d | 0 | g | 0 | d | 0 | d | 0 | b | 0 | c |
| 2 | Ametryn | 1.20 | 0 | a | 47 | e | 78 | cd | 95 | a | 77 | b | 92 | a | 87 | bc | 13 | cd | 95 | a-c | 97 | a | 97 | a-c | 97 | a | 83 | ab |
| 3 | Ametryn | 1.60 | 0 | a | 73 | cd | 82 | cd | 98 | a | 85 | ab | 80 | b | 75 | c | 20 | c | 83 | c-f | 80 | bc | 97 | a-c | 93 | a | 90 | ab |
| 4 | Ametryn | 2.40 | 0 | a | 65 | d | 88 | a-c | 95 | a | 85 | a | 87 | ab | 97 | ab | 30 | bc | 93 | a-d | 87 | a-c | 98 | ab | 90 | a | 75 | ab |
| 5 | Isoxaflutole + safener | 1.20 0.07 | 0 | a | 75 | cd | 97 | a | 97 | a | 98 | a | 93 | a | 100 | a | 43 | b | 97 | ab | 87 | a-c | 100 | a | 85 | a | 98 | a |
| 6 | Isoxaflutole + safener | 0.07 | 0 | a | 78 | bc | 95 | ab | 97 | a | 95 | ab | 87 | ab | 93 | ab | 47 | b | 93 | a-d | 77 | c | 93 | a-c | 87 | a | 98 | a |

Application timing: Applications preemergence broadcast to clean soil surface immediate after corn planting.

[1] DAT = days after treatment (application)

FIG. 7

| No. | Treatment | Formulation | Rate (lb ai/A) | Corn (% Injury) 21DAT[1] | | % Weed Control | | | | | | |
|---|---|---|---|---|---|---|---|---|---|---|---|---|
| | | | | | | Lambs-quarters 57DAT | | Giant Foxtail 57DAT | | Velvet-leaf 57DAT | | Redroot Pigweed 57DAT | |
| 1 | Untreated | | | 0 | a | 0 | e | 0 | d | 0 | c | 0 | d |
| 2 | Ametryn | 80% WDG | 1.20 | 0 | a | 73 | b-d | 77 | ab | 80 | a | 37 | c |
| 3 | Ametryn | 80% WDG | 1.60 | 0 | a | 77 | cd | 43 | c | 83 | a | 60 | a-c |
| 4 | Ametryn | 80% WDG | 2.40 | 0 | a | 80 | d | 60 | bc | 63 | b | 53 | bc |
| 5 | Ametryn | 80% WDG | 1.20 | | | | | | | | | | |
| | Isoxaflutole + safener | 2.0 SC | 0.07 | 0 | a | 100 | a-c | 80 | ab | 95 | a | 95 | ab |
| 6 | Isoxaflutole + safener | 2.0 SC | 0.07 | 0 | a | 100 | a-c | 73 | ab | 95 | a | 95 | ab |

Application timing: Preemergence broadcast to clean soil surface immediate after corn planting

[1] DAT = Days after treatment (application)

FIG. 8

| No. | Treatment | Formulation | Rate (lb ai/A) | Corn (% Injury) | | % Weed Control | | | | | | | |
|---|---|---|---|---|---|---|---|---|---|---|---|---|---|
| | | | | | | Velvetleaf | | Lambsquarters | | Redroot Pigweed | | Giant Foxtail | |
| | | | | 15DAT[1] | 44DAT | 44DAT | 71DAT | 44DAT | 71DAT | 44DAT | 44DAT | 44DAT | 71DAT |
| 1 | Untreated | | | 0 | 0 | 0 | 0 | 0 | 0 | 0 | 0 | 0 |
| 2 | AMV 5065 | 80% WDG | 1.20 | 0 | 0 | 0 | 0 | 27 | 37 | 27 | 0 | 17 |
| 3 | AMV 5065 | 80% WDG | 1.60 | 0 | 0 | 0 | 0 | 58 | 68 | 77 | 0 | 10 |
| 4 | AMV 5065 | 80% WDG | 2.40 | 0 | 0 | 0 | 0 | 52 | 52 | 53 | 0 | 0 |
| 5 | AMV 5065 | 80% WDG | 1.20 | 0 | 0 | 97 | 97 | 100 | 100 | 94 | 67 | 77 |
| 5 | Isoxaflutole + safener | 2.0 SC | 0.07 | | | | | | | | | |
| 6 | Isoxaflutole + safener | 2.0 SC | 0.07 | 0 | 0 | 100 | 100 | 100 | 100 | 98 | 72 | 83 |

Application timing: Application preemergence broadcast to clean soil surface immediate after corn planting

[1] DAT = Days after treatment (application)

FIG. 9

| No. | Treatment | Formu- lation | Rate (lb ai/A) | Corn (% Chlorosis) 21DAT[1] | | Corn (% Stunting) 26DAT | | Giant Foxtail 26DAT | | Lambs- quater 26DAT | | Giant Foxtail 40DAT | | Lambs- quarter 40DAT | | Giant Foxtail 54DAT | | Lamb- squarter 54DAT | | Giant Foxtail 82DAT | | Lambs- quarter 82DAT | | Yield (bu/acre) 9/15/10 | |
|---|---|---|---|---|---|---|---|---|---|---|---|---|---|---|---|---|---|---|---|---|---|---|---|---|---|
| | | | | | | | | | | | | | | | | % Weed Control | | | | | | | | | |
| 1 | Untreated | | | 0.0 | b | 0.0 | b | 0 | c | 0 | c | 0 | c | 0 | c | 0 | c | 0 | c | 0 | d | 0 | c | 62 | c |
| 2 | Ametryn | 80% WDG | 1.20 | 0.0 | b | 0.0 | b | 98 | ab | 67 | b | 87 | b | 100 | a | 75 | b | 100 | a | 68 | c | 100 | a | 131 | b |
| 3 | Ametryn | 80% WDG | 1.60 | 1.7 | b | 3.3 | b | 100 | a | 100 | a | 90 | b | 100 | a | 82 | b | 100 | a | 72 | c | 100 | a | 140 | ab |
| 4 | Ametryn | 80% WDG | 2.40 | 10.0 | a | 10.0 | a | 100 | a | 100 | a | 100 | a | 100 | a | 98 | a | 100 | a | 95 | ab | 100 | a | 138 | ab |
| 5 | Ametryn | 80% WDG | 1.20 | | | | | | | | | | | | | | | | | | | | | | |
| 5 | Isoxaflutole + safener | 2 SC | 0.07 | 0.0 | b | 1.7 | b | 100 | a | 100 | a | 98 | a | 100 | a | 98 | a | 100 | a | 93 | ab | 100 | a | 134 | b |
| 6 | Isoxaflutole + safener | 2 SC | 0.07 | 0.0 | a | 1.7 | b | 100 | a | 100 | a | 92 | b | 98 | ab | 92 | a | 90 | b | 85 | b | 90 | a | 136 | b |

Application timing: PRE = Preemergence right after planting

[1] DAT = Days after treatment (application)

FIG. 10

| No. | Treatment | Formu- lation | Rate (lb ai/A) | Corn (% Necrosis) 32DAT[1] | | Corn (% Injury) 60DAT | | % Weed Control | | | | | | | | | | | | | |
|---|---|---|---|---|---|---|---|---|---|---|---|---|---|---|---|---|---|---|---|---|---|
| | | | | | | | | Lambs- quarter 32DAT | | Velvet- leaf 32DAT | | Giant Foxtail 32DAT | | Lambs- quarter 60DAT | | Water- hemp 60DAT | | Velvet- leaf 60DAT | | Giant Foxtail 60DAT | |
| 1 | Untreated | | | 0 | c | 0 | a | 0 | b | 0 | b | 0 | b | 0 | c | 0 | d | 0 | f | 0 | d |
| 2 | Ametryn | 80% WDG | 1.20 | 9 | a | 0 | a | 95 | a | 92 | a | 95 | a | 70 | b | 70 | c | 51 | e | 55 | c |
| 3 | Ametryn | 80% WDG | 1.60 | 7 | ab | 0 | a | 95 | a | 95 | a | 95 | a | 70 | b | 73 | bc | 50 | e | 67 | bc |
| 4 | Ametryn | 80% WDG | 2.40 | 6 | ab | 0 | a | 95 | a | 95 | a | 95 | a | 77 | ab | 78 | b | 67 | cd | 85 | a |
| 5 | Ametryn | 80% WDG | 1.20 | | | 0 | a | 95 | a | 95 | a | 95 | a | 90 | a | 90 | a | 87 | a | 83 | a |
| 5 | Isoxaflutole + safener | 2.0 SC | 0.07 | 6 | ab | | | | | | | | | | | | | | | | |
| 6 | Isoxaflutole + safener | 2.0 SC | 0.07 | 4 | ab | 0 | a | 95 | a | 95 | a | 95 | a | 88 | a | 88 | a | 85 | a | 80 | ab |

Application timing: Application made preemergence broadcast to clean soil surface immediate after corn planting

[1] DAT = Days after treatment (application)

FIG. 11

| No. | Treatment | Formu-lation | Rate (lb ai/A) | Corn (% Injury) 14DAT[1] | | % Weed Control | | | | | |
|---|---|---|---|---|---|---|---|---|---|---|---|
| | | | | | | Velvet-leaf 49DAT | | Water-hemp 49DAT | | Green Foxtail 49DAT | |
| 1 | Untreated | | | 0 | a | 0 | f | 0 | c | 0 | c |
| 2 | Ametryn | 80% WDG | 1.20 | 0 | a | 50 | e | 92 | b | 90 | b |
| 3 | Ametryn | 80% WDG | 1.60 | 0 | a | 57 | e | 96 | a | 96 | a |
| 4 | Ametryn | 80% WDG | 2.40 | 0 | a | 87 | bc | 100 | a | 100 | a |
| 5 | Ametryn | 80% WDG | 1.20 | 0 | a | 100 | a | 100 | a | 100 | a |
| 5 | Isoxaflutole + safener | 2.0 SC | 0.07 | | | | | | | | |
| 6 | Isoxaflutole + safener | 2.0 SC | 0.07 | 0 | a | 100 | a | 100 | a | 99 | a |

Application timing: Application made preemergence broadcast to clean soil surface immediate after corn planting

[1] DAT = Days after treatment (application)

FIG. 12

METHOD FOR PRE-EMERGENT WEED CONTROL USING TRIAZINE-BASED HERBICIDE

CROSS-REFERENCE TO RELATED APPLICATIONS

This application claims the benefit of priority Application Ser. No. 61/557,277, filed on Nov. 8, 2011, which is expressly incorporated herein by reference in its entirety.

FIELD OF THE INVENTION

The invention relates to methods for pre-emergent weed control using triazine-based herbicides. More specifically, the invention relates to methods of applying a composition consisting essentially a triazine-based herbicide as a pre-emergence treatment to soil to control weed growth in crop plants.

INTRODUCTION

Triazine-based herbicides such as ametryn, atrazine, metribuzin, terbuthylazine, prometryn, propazine, simazine, trietazine, prometryn, desmetryn, terbutryne, terbumeton, and cyanazine inhibit photosynthesis and other enzymatic processes.

Particularly, Ametryn (or ametryne), 2-ethylamino-4-isopropylamino-6-methylthio-s-triazine, is conventionally for use as a post-emergent herbicide to control broadleaf weeds and annual grasses in certain crops, such as, pineapple, sugarcane, bananas, corn and potatoes. Yet, ametryn has never been shown nor demonstrated to be a pre-emergent herbicide in annual crops, such as cereals.

While post-emergent herbicides are effective at destroying established weeds, they are not typically effective at preventing weed growth. Likewise, pre-emergent herbicides may have a detrimental residual effect upon the emerging crops because most herbicides are not selective to the specific crops. Thus, it is surprising to discover that ametryn also can be used as an effective and safe pre-emergent herbicide with residual activity.

Weed control (both pre-emergence and post-emergence) is an important culture practice for crops growth. The term "culture" relates to situations of raising the crop, including soil aspects, seeding time, use of crop protection chemicals, agronomic system (conventional vs. minimum tillage, etc.).

SUMMARY OF THE INVENTION

Disclosed herein are methods for control of undesirable vegetation, comprising applying a composition consisting essentially of a triazine-based herbicide to the undesirable vegetation associated with a crop plant, the habitat of the crop plant, or a combination thereof, before emergence of the crop plant, wherein the crop plant is a cereal grain.

BRIEF DESCRIPTION OF THE FIGURES

The figures illustrate generally, by way of example, but not by way of limitation, various embodiments discussed in the present document.

FIG. 2 illustrates crop tolerance in a field trial according to an embodiment of the present invention.

FIG. 3 illustrates crop tolerance in a field trial according to an embodiment of the present invention.

FIG. 4 illustrates crop tolerance in a field trial according to an embodiment of the present invention.

FIG. 5 illustrates percent weed control in a field trial according to an embodiment of the present invention.

FIG. 6 illustrates percent weed control in a field trial according to an embodiment of the present invention.

FIG. 7 illustrates percent weed control in a field trial according to an embodiment of the present invention.

FIG. 8 illustrates percent weed control in a field trial according to an embodiment of the present invention.

FIG. 9 illustrates percent weed control in a field trial according to an embodiment of the present invention.

FIG. 10 illustrates percent weed control in a field trial according to an embodiment of the present invention.

FIG. 11 illustrates percent weed control in a field trial according to an embodiment of the present invention.

FIG. 12 illustrates percent weed control in a field trial according to an embodiment of the present invention.

DETAILED DESCRIPTION OF THE INVENTION

Figure 1:
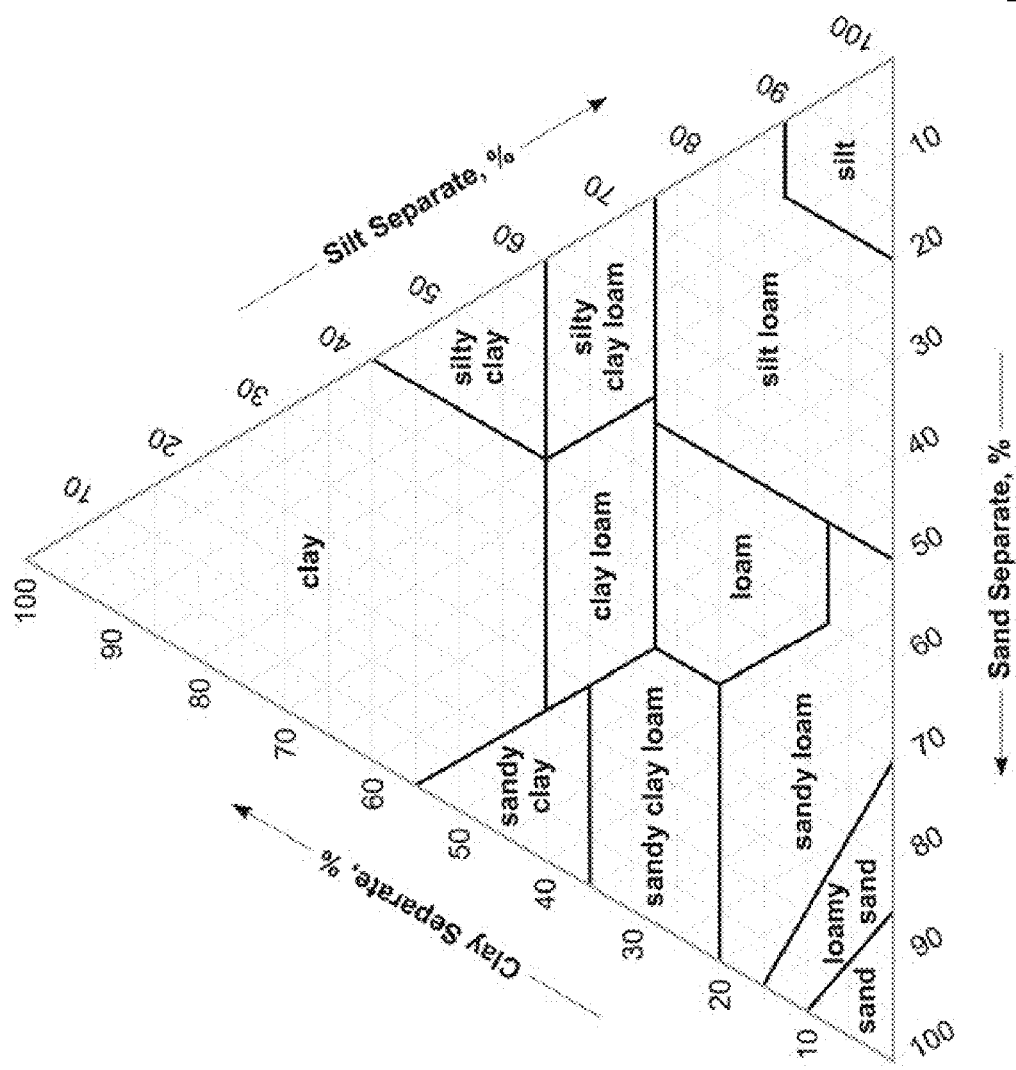
FIG. 1 is a schematic soil triangle demonstrating various soil textures suitable for use with various methods for pre-emergent weed control, according to embodiments of the present invention.

The invention relates to methods for pre-emergent weed control using triazine-based herbicides such as ametryn, atrazine, metribuzin, terbuthylazine, prometryn, propazine, simazine, trietazine, prometryn, desmetryn, terbutryne, terbumeton, and cyanazine. Particularly, methods of the present invention disclose herbicidal compositions to be applied to soil at early stages of the crop planting and growing process/cycle. For example, compositions consisting essentially of a triazine-based herbicide, e.g., ametryn, can be applied as a pre-emergent herbicide to control weeds significantly earlier in the cropping season than the labeled time for application in certain commercial products (e.g., Evik®, Gesapax®). Such commercial products label ametryn as a post-emergent herbicide for post-emergence control of broadleaf weeds and grasses in certain crops, where the treatments are applied after the weeds have emerged.

The methods for pre-emergent weed control using a composition consisting essentially of a triazine-based herbicide of the present invention are effective to injure the established undesirable vegetation and inhibit the emergence of a wide variety of both broadleaf and grassy weeds, while not significantly harming the germination and not inhibiting the growth of the desirable crop plants.

As used herein, the terms "pre-emergent" and "post-emergent" refer to the desirable crop plants, not to the undesirable vegetation to be controlled. Thus, the term "post-emergent," means the application of the herbicide composition to the crop plants that have emerged from the soil. The term "pre-emergent" means the application of the herbicide composition to a habitat, a weed, or soil, prior to the emergence of the crop plants from the soil.

As used herein, the term "weed control", or "control of undesirable vegetation" means that the herbicide compositions disclosed herein, when applied to a weed/undesirable vegetation, the habitat of a crop plant, or combination thereof, interferes with the normal growth and development of a weed. Examples of weed growth control activity include, but are not limited to, inhibition of root growth, inhibition of shoot growth, inhibition of shoot emergence, reduction of weed biomass inhibition of seed production, or reduce competitiveness of a weed for water, nutrients, or a combination thereof, that would otherwise be utilized by a crop plant or essentially competes with the crop thereby limiting yield. Alternatively, the herbicide compositions disclosed herein may be capable of controlling weeds by destroying/injuring them, and do not have any substantial injury effect on a crop plant for which growth is desired.

The present invention provides for pre-emergence weed control including applying to the soil a composition consisting essentially of a triazine-based herbicide. In certain embodiments, the herbicide composition consists essentially of one or more triazine-based herbicide(s). In certain embodiments, the herbicide composition consists essentially of ametryn.

The treatments may be applied before emergence of the crop plant, for example, prior to the planting of the crop plants, and between planting of the crop plant and emergence of the crop plant. In certain embodiments, triazine-based herbicide compositions may be applied to the soil at least about 5 days before planting a crop, at least about 15 days before planting a crop, or at least about 20 days before planting a crop. More specifically, the application treatments may be applied between about 5 days and about 60 days, between about 10 days and about 30 days, or between about 10 days and about 25 days prior to planting of the crop plant. Triazine-based herbicide compositions may also be applied multiple times to the soil before emergence of the crop plant. For example, triazine-based herbicide compositions may be applied to the soil one or more times before the planting of a corn crop, and then between planting and emergence of the crop plant. In certain embodiments, triazine-based herbicide compositions may be applied to the soil between about 5 days and about 60 days, between about 10 days and about 30 days, or between about 10 days and about 25 days prior to planting of the crop plant, and then again between planting of the crop plant and emergence of the crop plant. In one embodiment, triazine-based herbicide compositions may be applied to the soil at least about 21 days before the planting of a corn crop, and then again between planting of the crop plant and emergence of the crop plant.

Such pre-emergence application treatments of triazine-based herbicide compositions may be applied at a wide variety of concentrations and time intervals to the soil. Typically, the application treatments may be applied at a rate of from about 0.1 pound to about 3 pounds, from about 0.25 pound to about 2.4 pounds, or from about 0.5 pound to about 1.6 pounds of active ingredient per acre. Optimum application rates may vary depending on a variety of factors, such as, the hardiness of the particular weed species, weather, type of soil, and method of application. The specific rate of application can determine which crop species are tolerant to triazine-based herbicide, e.g., ametryn. For example, soybeans may show acceptable tolerance to ametryn at the lower end of the application rate ranges (e.g., 0.1-1.0 lb ai/a).

The condition of soil or soil texture can play an important role in herbicide performance or effectiveness of weed control. FIG. 1 is a schematic soil triangle demonstrating different soil textures resulting from the combination of various amounts the basic soil constituents of sand, silt or clay. The soil triangle classifies soils into various categories (i.e., soil textures) and can be used as a tool to determine the optimum rate for soil applied herbicides. Soil textures are classified by the fractions of each soil separate (sand, silt, and clay) present in a soil which can be completed by specific soil analysis laboratories using standard techniques well known in the art. Classifications are typically named for the primary constituent particle size or a combination of the most abundant particles sizes, e.g. "sandy clay" or "silty clay." A fourth term, loam, is used to describe a roughly equal concentration of sand, silt, and clay, and leads to the naming of even more classifications, e.g. "clay loam" or "silt loam." Although an arbitrary classification system, this can be an extremely simple and effective means to rapidly assess and classify a soil's physical condition. Coarse textured soils ("light" soils) typically require lower rates of preemergence herbicides while finer soils ("heavy" soils) often require a higher amount of herbicide for equivalent weed control. The amount of organic matter present in the soil can further modify higher or lower the optimum amount of herbicide needed.

Methods for pre-emergent weed control of the present invention are effective in various types of soil including silt, sand, clay and mixtures thereof. More specifically, the present invention provides effective weed control in soil types comprising components such as clay, sandy clay, clay loam, silty clay, silty, clay loam, sandy clay loam, loam, sandy loam, loamy sand, sand, silt loam and silty. FIG. 1 is a schematic soil triangle demonstrating different soil textures resulting from the combinations of various amounts/percentages of different soil types. Typically, soils comprising 50% or more of the sand by weight are classified as sandy. Silty soils have particles that are intermediate in size between sand and clay and generally are comprised of 40-100% silt. Clay soils are fine-textured soils containing small particles and soil pores, typically including between 35 and 40 percent clay. In certain embodiments, methods for pre-emergent weed control provide effective weed control in light textured soil (i.e., coarse or sandy soils) such as sandy loam and loamy sand. In certain embodiments, methods for pre-emergent weed control provide effective weed control in medium textured soil (i.e., with high percentages of clay and silt), such as loam, silt loam, silt, silty clay loam, clay loam. Certain embodiments provides effective pre-emergent weed control in fine textured soil, such as clay, clay loam, sandy clay, sandy clay loam, silty clay, silty clay, and loam.

The concentration of traizine-based herbicide in the composition for pre-emergence application treatments can be expressed in percentage. The percentage, by weight (or "weight percent"), of a traizine-based herbicide in the composition of the present invention can vary. In certain embodiments, when the composition is in water dispersible granule (WDG) form, the percentage by weight of a traizine-based herbicide in the composition is between 60% and 95%, between 70% and 95%, and between 80% and 90%. In certain embodiments, when the composition is in liquid form, the percentage by weight of a traizine-based herbicide in the composition is between 40% and 60%, between 45% and 55%, and between 48% and 52%.

Methods of the pre-emergent weed control of the present invention include application to fields (or habitats) comprising transgenic hybrids. These fields may be planned to produce a transgenic hybrid, or have been planted to transgenic hybrids, such as transgenic corn hybrids. Contemplated transgenic hybrids include hybrids with traits relating to herbicide tolerance, insect resistance, drought tolerance, salt tolerance, health benefit, and combinations thereof. In certain embodiments, herbicide tolerant traits include hybrids tolerant to glyphosate, glufosinate-p, imazethapyr, imazaquin, acetolactate synthase inhibitors (ALS) (also known as acetohydroxy-acid synthase inhibitors (AHAS)), and HPPD (p-hydroxyphenylpyruvate dioxygenase) inhibitors which includes topramazone, mesotrione, tembotrione and other members of this mode of action of herbicides. In certain embodiments, insect resistance traits include in-plant protection to both below ground and above ground insect pests such as corn rootworm, European corn borer, cutworms, corn earworm, Western bean cutworm, and mixtures thereof.

Methods for pre-emergent weed control according to the present invention include applying the herbicide to fields (or habitats) using various tillage systems, including no-tillage, minimum tillage, conservation tillage, conventional tillage.

Methods for pre-emergent weed control of the present invention are capable of controlling undesirable vegetation growing in the habitat of crop plants, particular cereal grains, such as, corn, rice, sorghum, and wheat, without damaging the crop plants. In certain embodiments, the crop plant includes corn, such as, but is not limited to, field corn (maize), sweet corn, white corn, silage corn, calico corn, popcorn, corn bundles, Indian corn, and broom corn.

In certain embodiments, methods of the pre-emergent weed control of the present invention may be capable of controlling undesirable vegetation growing in corn, such as field corn. In certain embodiments, the corn is transgenic. Such transgenic corn may have a trait such as herbicide tolerance, insect resistance, drought tolerance, a salt tolerance, a health benefit, and mixtures thereof. In one embodiment, the herbicide tolerance is tolerance to a herbicide such as glyphosate, glufosinate-p, imazethapyr, imazaquin, and amino acid synthesis inhibitors. In one embodiment, the insect resistance comprises in-plant protection to an above ground and below ground insect pest. In further embodiments, the insect pest may include corn rootworm, European corn borer, cutworms, corn earworm, Western bean cutworm, and mixtures thereof.

Methods for pre-emergent weed control according to the present invention can be used for many different kinds and heights of undesirable vegetation or weeds, including winter annuals, small grasses, annual grasses and broadleaf weeds.

Specific non-limiting examples of broadleaf weeds include Velvetleaf, Flossflower, Redroot Pigweed, Palmer Amaranth, Powell Amaranth, Common Pigweed, crosses of Pigweed species (Pigweeds), Spiny Amaranth, Waterhemp (e.g., Tall Waterhemp), Common Ragweed, Giant Ragweed, Bidens, Erect Spiderling, Wild Mustard, Purse Shepherds, Spurge spp., Prostrate Spurge, Spurge, Common Lambsquarters, Canada Thistle, Possum Grape, Hairy Clidemia, Dayflower, Horseweed, Swinecress, Melon, Tansymustard, Drymary, Malayan Fireweed, Mexican Fireplant, Soldier Shaggy, Annual Sunflower, Morningglory spp, Kochia, Prickly Lettuce, Henbit, Pink Cheeseweed, Bitter Balsamapple, Plantain species, Southern Smartweed, Pennsylvania Smartweed, Common Purslane, Spiked Elephantfoot, Florida Pusley, Brazil Pusley, Dock, Black Nightshade, Eastern Black Nightshade, Sida, Jim Hill Mustard, Nightshade spp., Annual Sowthistle, Common Chickweed, Ladino Clover, Speedwell, Wedelia, and Common Cocklebur.

Specific non-limiting examples of grasses and sedges includes Fall Panicum, Quackgrass, Wild Garlic, Texas Panicum Brachiaria, Cheatgrass, Black Flatsedge, Purple Nutsedge, Yellow Nutsedge, Crabgrass, Junglerice, Barnyardgrass, Millets, Goosegrass, Tall Fescue, Indian murainagrass, Mexican Grass, Red Sprangletop, Guinea Grass, Rivergrass, Annual Bluegrass, Itchgrass, Giant Foxtail, Yellow Foxtail, Green Foxtail, crosses of *Setaria* species (Foxtails), and Browntop Panicum, Wild Oats.

In certain embodiments, methods of the present invention may control weeds, such as, Little barley, Shepherd's purse, Cressleaf groundsel, Common groundsel, Horseweed (Marestail), Gray goldenrod, Common chickweed, Yellow rocket, Horsetail, Purple deadnettle, Dandelion, Corn speedwell, Purslane speedwell, Virginia pepperweed, Giant ragweed, Common yellow oxalis, Wild mustard, Italian ryegrass, Fanweed, Common lambsquarters, Annual bluegrass, Large crabgrass, Foxtail spp, Giant foxtail, Green foxtail, Large crabgrass, Barnyardgrass, Italian ryegrass, Common lambsquarters, Redroot pigweed, Waterhemp, Palmer amaranth, Common ragweed, Giant ragweed, Cocklebur, Velvetleaf, and Morningglory spp., Goosegrass, and mixtures thereof.

In certain embodiments, methods of the present invention may be used to control or render less competitive weeds of various heights depending on the weed species growing or associated with the crops. These weeds may be present at the time of application or germinate after the time of application. For example, triazine-based herbicides of the present invention may be applied to weeds with heights of less than about 12 inches. Typically, methods of the present invention may provide at least 50%, 60%, 70%, 80%, 85%, 90%, 95%, 97%, 99%, or 100% weed control when the weed heights are less than about 12 inches. In certain embodiments, methods of the present invention may provide at least 80%, 85%, 90%, 95%, 97%, 99%, or 100% weed control when the weed heights are less than about 2 inches. In certain embodiments, methods of the present invention may provide at least 50%, 60%, 70%, 80%, 85%, 90%, 95%, 97%, 99%, or 100% weed control to prevent germination of weeds (i.e., weeds that are not present at application but which would otherwise germinate if untreated).

Contemplated triazine-based herbicides and their salts, including ametryn and their salts, may be applied in any suitable manner or form recognized by the art, such as dry, powder or dusting powder, slurry, liquid, granule, suspension, dispersion, diluted liquid or nebulized spray. In those instances where the herbicide composition is diluted or in liquid/slurry/nebulized form, it may be diluted with any suitable solvent depending on the application and any constituents that have been mixed with the herbicide compositions either with or without water as a carrier. Contemplated solvents include any suitable pure or mixture of organic molecules that are volatilized at a desired temperature, such as the critical temperature, or that can facilitate any of the above-mentioned design goals or needs. The solvent may also include any suitable pure or mixture of polar and non-polar compounds. As used herein, the term "pure" means that component that has a constant composition. For example, pure water is composed solely of $H_2O$. As used herein, the term "mixture" means that component that is not pure, including salt water. As used herein, the term "polar" means that characteristic of a molecule or compound that creates an unequal charge, partial charge or spontaneous charge distribution at one point of or along the molecule or compound. As used herein, the term "non-polar" means that characteristic of a molecule or compound that creates an equal charge, partial charge or spontaneous charge distribution at one point of or along the molecule or compound.

In certain embodiments, the solvent or solvent mixture (i.e., including at least two solvents) comprises solvents that are considered part of the hydrocarbon family of solvents. Hydrocarbon solvents contain carbon and hydrogen, and a majority of hydrocarbon solvents are non-polar, while a few hydrocarbon solvents could be considered polar. Hydrocarbon solvents are generally broken down into three classes: aliphatic, cyclic and aromatic. Aliphatic hydrocarbon solvents may include both straight-chain compounds and compounds that are branched and possibly crosslinked, yet aliphatic hydrocarbon solvents are not considered cyclic. Cyclic hydrocarbon solvents include at least three carbon atoms oriented in a ring structure with properties similar to aliphatic hydrocarbon solvents. Aromatic hydrocarbon solvents include generally three or more unsaturated bonds with a single ring or multiple rings attached by a common bond and/or multiple rings fused together. Contemplated hydrocarbon solvents include toluene, xylene, p-xylene, m-xylene, mesitylene, solvent naphtha H, solvent naphtha A, alkanes, such as pentane, hexane, isohexane, heptane, nonane, octane, dodecane, 2-methylbutane, hexadecane, tridecane, pentadecane, cyclopentane, 2,2,4-trimethylpentane, petroleum ethers, halogenated hydrocarbons, such as chlorinated hydrocarbons, nitrated hydrocarbons, benzene, 1,2-dimethylbenzene, 1,2,4-trimethylbenzene, mineral spirits, kerosine, isobutylbenzene, methylnaphthalene, ethyltoluene, ligroine. Particularly contemplated solvents include, but are not limited to, pentane, hexane, heptane, cyclohexane, benzene, toluene, xylene and mixtures or combinations thereof.

In certain embodiments, the solvent or solvent mixture may comprise solvents that are not considered part of the hydrocarbon solvent family of compounds, such as ketones, acetone, diethyl ketone, methyl ethyl ketone and the like, alcohols, esters, ethers and amines. In yet certain embodiments, the solvent or solvent mixture may include a combination of any of the solvents disclosed herein.

In certain embodiments, adjuvants may be added to contemplated herbicides and tank mixtures to improve the control of undesirable vegetation, i.e., emerged weeds. Contemplated adjuvants include non-ionic surfactants, crop oils, crop oil concentrates, methylated seed oils, high surfactant oil concentrates, and adjuvant products containing these components.

All applications, publications, patents and other references, citations cited herein are incorporated by reference in their entirety. In case of conflict, the specification, including definitions, will control.

As used herein, the singular forms "a", "and," and "the" include plural referents unless the context clearly indicates otherwise.

As used herein, all numerical values or numerical ranges include integers within such ranges and fractions of the values or the integers within ranges unless the context clearly indicates otherwise. Thus, for example, reference to a range of from 5 days to 60 days includes from 5 days, 6 days, . . . , 58 days, 59 days, and 60 days.

A number of embodiments of the invention have been described. Nevertheless, it will be understood that various modifications may be made without departing from the spirit and scope of the invention. Accordingly, the following examples are intended to illustrate but not limit the scope of invention described in the claims.

To illustrate the invention, specific examples are set forth below. The following examples are merely illustrative of the present invention and should not be considered as limiting the scope of the invention in any way, as these examples and other equivalents thereof will become apparent to those skilled in the art in light of the present invention and the accompanying claims.

EXAMPLES

Materials and Methods

Several scientific and replicated field research trials were conducted in multiple locations to evaluate weed control and crop tolerance of herbicide compositions containing about 80% by weight of ametryn active ingredient in the form of a water dispersible granule (WDG). The herbicide compositions were applied to the soil surface with or without weeds present at specific intervals i) before planting (preplant), ii) prior to planting and incorporated into the soil (preplant incorporated), and iii) after planting of the corn, but prior to emergence (preemergence).

Small plot research trials were conducted using a statistical design known as Randomized Complete Block Design (RCBD), which assumes that a population of experimental units can be divided into a number of relatively homogeneous subpopulations or blocks. The treatments are then randomly assigned to experimental units such that each treatment occurs equally often (usually once) in each block—i.e., each block contains all treatments. Blocks usually represent levels of naturally occurring differences or sources of variation that are unrelated to the treatments. In the analysis, the variation among blocks can be partitioned out of the experimental error (MSE), thereby reducing this quantity and increasing the power of the test. See, Clewer, A. G., and D. H. Scarisbrick. 2001. Practical statistics and experimental design for plant and crop science. John Wiley & Sons Ltd., New York. crop science. Treatment size was typically 4 rows of corn on 30-inch row spacing×30 feet long replicated 3 to 4 times. Preplant, preplant incorporated (PPI), or preemergence (PRE) treatments were uniformly applied with a hand-held backpack sprayer pressurized with compressed air or carbon dioxide ($CO_2$) as the propellant to simulate commercial scale application. Treatments were applied using flat fan nozzle or spray nozzles at from 30 to 35 pounds per square inch (psi) delivering from 15 to 20 gallons of finished spray solution per acre.

Efficacy on weeds and crop tolerance evaluations were conducted at specified intervals for each trial. Ametryn herbicide (80% WDG) was applied to the soil at the times relative to planting as indicated at rates of 0.8, 1.2, 1.6, and 2.4 pounds of active ingredient per acre (lb ai/a) at various days preplant up to right before planting (0 day preplant), or immediately following planting (PRE), but before crop emergence. Crop tolerance was evaluated at intervals of 7 to 14, 21 to 28, and 42 to 56 days after corn emergence in these trials. Crop injury, if observed, was reported on a 0 to 100% visual rating scale and the type of injury (e.g., stunting) was noted. The efficacy of ametryn at a rate of 0.8, 1.2, 1.6 and 2.4 lbs ai/a applied 7 to 14 days preplant was evaluated on grass and broadleaf weeds at intervals of 7 to 14, 21 to 28, and 42 to 56 days after corn emergence. Efficacy trials were also conducted in no tillage and reduced tillage cropping systems, allowing for evaluations of existing weeds at application (i.e., burndown) and residual control of weeds which germinate following application. In an additional trial, efficacy of ametryn at rates of 1.2, 1.6 and 2.4 lb ai/a applied PRE was evaluated on grass and broadleaf weeds at the same intervals as the earlier trials. Efficacy in the later trials was conducted in both conventional and reduced tillage systems, which allowed for evaluations of residual weed control following application. A local commercial corn hybrid was planted in each trial location.

In the FIGS. 2-12, the means within each column that are followed by the same letter (e.g., a, b, c, d, e, and f) do not significantly differ (P=0.05, Student-Newman-Keuls).

Example 1

A crop tolerance (corn) field trial was conducted in Springfield, Nebr. on medium textured soil. Ametryn herbicide (80% WDG) was applied to bare ground, preplant, prior to emergence at rates of 0.8, 1.6, and 2.4 pounds of active ingredient per acre (lb ai/a) 12 days preplant, right before planting (0 day preplant), and immediately following planting (PRE). The application water volume was 20 gallons per acre. Crop tolerance was evaluated at intervals of 23, 33, 41 and 56 days after corn emergence in these trials. FIG. 2 shows the crop tolerance (corn) field data. Corn injury (height of corn, number of plants emerged) was measured as visual injury (% injury) at three different times during the season. No injury to corn was observed from all three pre-emergence application timings.

Example 2

A crop tolerance (corn) field trial was conducted in Laurel, Md. on a light soil. Ametryn herbicide (80% WDG) was applied to the soil immediately after planting at rates of 0.8, 1.6, and 2.4 pounds of active ingredient per acre (lb ai/a) 14 days preplant, 2 days preplant, and immediately following planting (PRE). The application volume was 20 gallons per acre. Crop tolerance was evaluated at intervals of 14, 21 and 27 days after corn emergence in these trials. FIG. 3 summarizes the crop tolerance (corn) field data. The data shows that there was non-significant or no injury to corn when the application treatments were made at 14 days before planting. Further, there was non-significant or no injury to corn when the application treatments were made at 2 days before planting at 0.8 and 1.6 lb ai/a. It is important to note that even though visual injury was measured at certain times, there was generally no reduction in yield. Generally, less than 10% visual injury is not considered significant to the corn grower, as long as yields are not affected.

Example 3

A crop tolerance (corn) field trial was conducted in Camden, N.C. on a light textured soil. Ametryn herbicide (80% WDG) was applied preemergence to bare soil at rates of 0.8, 1.6, and 2.4 pounds of active ingredient per acre (lb ai/a) 11 days preplant, right before planting (0 day preplant), and immediately following planting (PRE). The application volume was 20 gallons of water per acre. Crop tolerance was evaluated at intervals of 15, 29 and 41 days after corn emergence in these trials. FIG. 4 summarizes the crop tolerance (corn) field data. No injury to corn was observed from all three pre-emergence application timings.

Example 4

A weed control field trial was conducted in Laurel, Md. in on a light textured soil. Ametryn herbicide (80% WDG) was applied to bare soil in the field to Goosegrass and Lambsquaters at rates of 0.8, 1.6, and 2.4 pounds of active ingredient per acre (lb ai/a) 14 days preplant, 2 days preplant, and immediately following planting (PRE). The application volume was 20 gallons per acre. Percent weed control was evaluated at intervals of 21 and 35 days after corn emergence in these trials. FIG. 5 summarizes the percent weed control. The field data demonstrates significant improvement of weed control over the untreated treatment (control field).

Example 5

A weed control field trial was conducted in Laurel, Md. on a light textured soil. Ametryn herbicide (80% WDG) was applied preemergence to bare soil in the field to Giant Foxtail, Velvetleaf, Waterhemp, Giant Ragweed, Morningglory, and Cocklebur at rates of 1.2, 1.6 and 2.4 pounds of active ingredient per acre (lb ai/a) immediately following planting (PRE) and prior to corn emergence. The application volume was between 15 and 25 gallons per acre. Percent weed control was evaluated at intervals of 27 and 56 days after corn emergence in these trials. FIG. 6 summarizes the percent weed control. The field data demonstrates significant improvement of weed control over the untreated treatment (control field).

Example 6

A weed control field trial was conducted in Richland, Iowa on a fine textured soil (e.g., silty clay loam). Three examples of herbicide compositions were used and compared i) ametryn herbicide (80% WDG), i.e., Nos. 2-4, ii) mixture of ametryn herbicide (80% WDG) and isoxaflutole with a corn safener (cyprosulfamide), i.e., No. 5, or iii) isoxaflutole with a corn safener (cyprosulfamide), i.e., No. 6, were applied to clean soil surface in the field to Giant Foxtail, Velvetleaf, Waterhemp, Giant Ragweed, Morningglory, and Cocklebur at rates of 1.2, 1.6, 2.4, 1.2+0.07, and 0.07 pounds of active ingredient per acre (lb ai/a) immediately following planting (PRE) and prior to corn emergence. The application volume was 20 gallons per acre. Percent weed control was evaluated at intervals of 27 and 56 days after corn emergence in these trials. FIG. 7 summarizes the percent weed control. The percent corn injury data demonstrates that the preemergence application of ametryn herbicide at all the tested rates provided excellent corn safety when evaluated at 11 days after application, and was comparable to the commercial standard herbicide of isoxaflutole with safener. Pre-emergence treatment of ametryn provided moderate to good control of giant foxtail, velvetleaf, giant ragweed, cocklebur, and morningglory and excellent control of Waterhemp at 4 weeks observation after application. This level of control was generally statistically equivalent to the commercial standard treatment.

Example 7

A weed control field trial was conducted in Wyoming, Ill. on a medium textured soil (e.g., silt loam). Three examples of herbicide compositions were used and compared. i) ametryn herbicide (80% WDG), i.e., Nos. 2-4, ii) mixture of ametryn herbicide (80% WDG) and isoxaflutole with a corn safener (cyprosulfamide), i.e., No. 5, or iii) isoxaflutole with a corn safener (cyprosulfamide), i.e., No. 6, were applied to clean soil surface in the field to Lambsquarters, Giant Foxtail, Velvetleaf, and Redroot Pigweed at rates of 1.2, 1.6, 2.4, 1.2+ 0.07, and 0.07 pounds of active ingredient per acre (lb ai/a) immediately following planting (PRE) and prior to corn emergence. The application volume was 20 gallons per acre. Percent weed control was evaluated at 57 days after corn emergence in these trials. FIG. 8 summarizes the percent weed control. The percent corn injury data demonstrates that the preemergence application of ametryn herbicide at all the tested rates provided excellent corn safety when evaluated at 21 days after application, and was comparable to the commercial standard herbicide of isoxaflutole with safener. Preemergence treatment of ametryn provided good control of Lambsquarters, Giant Foxtail, Velvetleaf, and Redroot Pigweed at 8 weeks observation after application. This level of control was statistically equivalent to the commercial standard treatment.

Example 8

A weed control field trial was conducted in Fishers, Ind. on a fine textured soil (e.g., clay loam). Three examples of herbicide compositions were used and compared. i) ametryn herbicide (80% WDG), i.e., Nos. 2-4, ii) mixture of ametryn herbicide (80% WDG) and isoxaflutole with a corn safener (cyprosulfamide), i.e., No. 5, or iii) isoxaflutole with a corn safener (cyprosulfamide), i.e., No. 6, were applied to clean soil surface in the field to Velvetleaf, Lambsquarters, Ragweed Pigweed, and Giant Foxtail, at rates of 1.2, 1.6, 2.4, 1.2+0.07, and 0.07 pounds of active ingredient per acre (lb ai/a) immediately following planting (PRE) and prior to corn emergence. The application volume was 19.5 gallons per acre. Percent weed control was evaluated at 44 and 71 days after corn emergence in these trials. FIG. 9 summarizes the percent weed control. The percent corn injury data demonstrates that the preemergence application of ametryn herbicide at rates up to 2.4 lbs ai/a preemergence provided excellent safety to corn at 15 days and 44 days after application, and was comparable to the commercial standard herbicide of isoxaflutole with safener. Pre-emergence treatment of ametryn provided moderate weed control of Giant Foxtail and Velvetleaf, and good weed control of Lambsquarters and Redroot Pigweed, at the rate of 1.6 lb ai/a. Pre-emergence treatment of isoxaflutole with cyprosulfamide provided good control of broadleaf species and moderate control of giant foxtail, and was superior to ametryn in this trial.

Example 9

A weed control field trial was conducted in Laurel, Md. on a light textured soil. Three examples of herbicide compositions were used and compared. i) ametryn herbicide (80% WDG), i.e., Nos. 2-4, ii) mixture of ametryn herbicide (80% WDG) and isoxaflutole with a corn safener (cyprosulfamide), i.e., No. 5, or iii) isoxaflutole with a corn safener (cyprosulfamide), i.e., No. 6, were applied to clean soil surface in the field to Velvetleaf, Lambsquarters, Ragweed Pigweed, and Giant Foxtail, at rates of 1.2, 1.6, 2.4, 1.2+0.07, and 0.07 pounds of active ingredient per acre (lb ai/a) immediately following planting (PRE) and prior to corn emergence. The application volume was 20 gallons per acre. Percent weed control was evaluated at 26, 40, 54, and 82 days after corn emergence in these trials. FIG. 10 summarizes the percent weed control. The percent corn injury data demonstrates that the preemergence application of ametryn herbicide at rates up to 1.6 lbs ai/a was as safe to corn as a commercial standard of isoxaflutole with cyprosulfamide on a very light soil. Minor injury was observed at the higher rate, e.g., 2.4 lb ai/a. It is important to note that the maximum rates would be adjusted downward on a coarse textured soil. Pre-emergence treatment of ametryn at all tested rates provided excellent safety to corn at 26, 40, 54 and 82 days after application. Even when minor injury was observed there was no negative effect on yield.

Example 10

A weed control field trial was conducted in Geneva, Minn. on a medium textured soil (e.g., sandy clay loam). Three examples of herbicide compositions were used and compared. i) ametryn herbicide (80% WDG), i.e., Nos. 2-4, ii) mixture of ametryn herbicide (80% WDG) and isoxaflutole with a corn safener (cyprosulfamide), i.e., No. 5, or iii) isoxaflutole with a corn safener (cyprosulfamide), i.e., No. 6, were applied to clean soil surface in the field to Lambsquarters, Velvetleaf, Giant Foxtail, Waterhemp (e.g., Tall Waterhemp), and at rates of 1.2, 1.6, 2.4, 1.2+0.07, and 0.07 pounds of active ingredient per acre (lb ai/a) immediately following planting (PRE) and prior to corn emergence. The application volume was from 15 to 25 gallons per acre. Percent weed control was evaluated at 32 and 60 days after corn emergence in these trials. FIG. 11 summarizes the percent weed control. The percent corn injury data demonstrates that the preemergence application of ametryn herbicide at all tested rates provided acceptable safety to corn when evaluated at 32 and 60 days after application. Slight injury to corn, in the form of necrosis, was observed in all treatments at 32 days evaluation. Pre-emergence treatment of ametryn provided good control of Velvetleaf, Giant Foxtail, and Lambsquarters at 32 days after application, and moderate control of Waterhemp at 60 days after application.

Example 11

A weed control field trial was conducted in York, Nebr. on a medium textured soil (e.g., silt loam). Three examples of herbicide compositions were used and compared. i) ametryn herbicide (80% WDG), i.e., Nos. 2-4, ii) mixture of ametryn herbicide (80% WDG) and isoxaflutole with a corn safener (cyprosulfamide), i.e., No. 5, or iii) isoxaflutole with a corn safener (cyprosulfamide), i.e., No. 6, were applied to clean soil surface in the field to Velvet-leaf, Waterhemp, and Giant Foxtail at rates of 1.2, 1.6, 2.4, 1.2+0.07, and 0.07 pounds of active ingredient per acre (lb ai/a) immediately following planting (PRE) and prior to corn emergence. The application volume was from 20 gallons per acre. Percent weed control was evaluated at 49 days after corn emergence in these trials. FIG. 12 summarizes the percent weed control. The percent corn injury data demonstrates that the preemergence application of ametryn herbicide at all tested rates provided acceptable safety to corn when evaluated at 14 days after application, and was comparable to the commercial standard herbicide of isoxaflutole with safener. Pre-emergence treatment of ametryn provided good control of Green Foxtail and Waterhemp, and moderate control of Velvetleaf, at 4 weeks after application. Pre-emergence treatment of isoxaflutole with safener provided similar control of Green Foxtail and Waterhemp, and superior control of velvetleaf, at 4 weeks after application. Control of all weed species at 7 weeks after application was excellent.

What is claimed is:

1. A herbicidal method for control of undesirable vegetation in a crop plant, consisting essentially of applying a herbicidally effective amount of a composition consisting essentially of a single herbicide being ametryn as the only active ingredient to the undesirable vegetation associated with the crop plant, the habitat of the crop plant, or a combination thereof before emergence of the crop plant, wherein the single herbicide is applied at a rate of from about 0.1 to about 3 pounds of active ingredient per acre (lb ai/a), wherein the crop plant is a corn.

2. The method of claim 1, wherein the applying occurs between about 5 days and about 60 days prior to planting of the crop plant.

3. The method of claim 1, wherein the applying occurs between about 10 days and about 30 days prior to planting of the crop plant.

4. The method of claim 1, wherein the applying occurs between about 10 days and about 25 days prior to planting of the crop plant.

5. The method of claim 2, wherein the applying further occurs between planting of the crop plant and emergence of the crop plant.

6. The method of claim 1, wherein the corn is selected from the group consisting of field corn (maize), sweet corn, white corn, silage corn, calico corn, popcorn, corn bundles, Indian corn, and broom corn.

7. The method of claim 1, wherein the corn is transgenic.

8. The method of claim 7, wherein the transgenic corn has a trait selected from the group consisting of herbicide tolerance, insect resistance, drought tolerance, salt tolerance, a health benefit, and mixtures thereof.

9. The method of claim 8, wherein the herbicide tolerance is tolerance to a herbicide selected from the group consisting of glyphosate, glufosinate-p, imazethapyr, imazaquin, and amino acid synthesis inhibitors.

10. The method of claim 8, wherein the insect resistance comprises in-plant protection to an above ground and below ground insect pest.

11. The method of claim 10, wherein the insect pest is selected from the group consisting of corn rootworm, European corn borer, cutworms, corn earworm, Western bean cutworm, and mixtures thereof.

12. The method of claim 1, wherein the undesirable vegetation comprises a weed.

13. The method of claim 12, wherein the weed comprises a grass and/or sedge weed.

14. The method of claim 12, wherein the weed comprises a broadleaf weed.

15. The method of claim 13, wherein the grass weed is selected from the group consisting of Fall Panicum, Quackgrass, Wild Garlic, Texas Panicum Brachiaria, Cheatgrass, Black Flatsedge, Purple Nutsedge, Yellow Nutsedge, Crabgrass, Junglerice, Barnyardgrass, Millets, Goosegrass, Tall Fescue, Indian murainagrass, Mexican Grass, Red Sprangletop, Guinea Grass, Rivergrass, Annual Bluegrass, Itchgrass, Giant Foxtail, Yellow Foxtail, Green Foxtail, crosses of *Setaria* species (Foxtails), Browntop Panicum, and Wild Oats.

16. The method of claim 14, wherein the broadleaf weed is selected from the group consisting of Velvetleaf, Flossflower, Redroot Pigweed, Palmer Amaranth, Powell Amaranth, Common Pigweed, crosses of Pigweed species (Pigweeds), Spiny Amaranth, Waterhemp, Common Ragweed, Giant Ragweed, Bidens, Erect Spiderling, Wild Mustard, Purse Shepherds, Spurge spp., Prostrate Spurge, Spurge, Common Lambsquarters, Canada Thistle, Possum Grape, Hairy Clidemia, Dayflower, Horseweed, Swinecress, Melon, Tansymustard, Drymary, Malayan Fireweed, Mexican Fireplant, Soldier Shaggy, Annual Sunflower, Morningglory species, Kochia, Prickly Lettuce, Henbit, Pink Cheeseweed, Bitter Balsamapple, Plantain species, Southern Smartweed, Pennsylvania Smartweed, Common Purslane, Spiked Elephantfoot, Florida Pusley, Brazil Pusley, Dock, Black Nightshade, Eastern Black Nightshade, Sida, Jim Hill Mustard, Nightshade spp., Annual Sowthistle, Common Chickweed, Ladino Clover, Speedwell, Wedelia, and Common Cocklebur.

17. The method of claim 1, wherein the composition is in water dispersible granule form.

18. The method of claim 17, wherein the ametryn is present in the water dispersible granule composition in an amount from 60% to 95% by weight.

19. The method of claim 1, wherein the composition is in liquid form.

20. The method of claim 19, wherein the ametryn is present in the liquid composition in an amount from 40% to 60% by weight.

21. The method of claim 1, wherein the herbicide is applied to a soil type selected from the group consisting of light textured soil, medium textured soil, and fine textured soil.

22. The method of claim 1, wherein the composition has an adjuvant.

23. The method of claim 22, wherein the adjuvant is selected from the group consisting of non-ionic surfactants, crop oils, crop oil concentrates, methylated seed oils, high surfactant oil concentrates, and mixtures thereof.

24. The method of claim 1, wherein the habitat comprises a tillage system.

25. The method of claim 24, wherein the tillage system is selected from the group consisting of no-tillage, conservation tillage, minimum tillage and conventional tillage.

26. A herbicidal method for control of undesirable vegetation in a crop plant, consisting essentially of applying between about 5 days and about 60 days prior to planting of a corn a herbicidally effective amount of a composition consisting essentially of a single herbicide being ametryn as the only active ingredient to the undesirable vegetation associated with the corn, the habitat of the corn, or a combination thereof before emergence of the corn; wherein the single herbicide is applied at a rate of from about 0.1 to about 3 pounds of active ingredient per acre (lb ai/a).

27. The method of claim 26, wherein the applying occurs between 10 days and about 25 days prior to planting of the corn.

28. The method of claim 26, wherein the applying further occurs between planting of the corn and emergence of the corn.

29. The method of claim 26, wherein the corn is selected from the group consisting of field corn (maize), sweet corn, white corn, silage corn, calico corn, popcorn, corn bundles, Indian corn, and broom corn.

30. A herbicidal method for control of a weed in a crop plant, consisting essentially of applying at about 21 days prior to planting of a corn a herbicidally effective amount of a composition consisting essentially of a single herbicide being ametryn as the only active ingredient to the undesirable vegetation associated with the corn, the habitat of the corn, or a combination thereof before emergence of the corn; wherein the single herbicide is applied at a rate of from about 0.1 to about 3 pounds of active ingredient per acre (lb ai/a).

31. The method of claim 30, wherein the weed is a grass weed.

32. The method of claim 30, wherein the weed is a broadleaf weed.

* * * * *